(12) United States Patent
Dubois et al.

(10) Patent No.: US 7,582,671 B2
(45) Date of Patent: Sep. 1, 2009

(54) THERAPEUTIC USE OF N-(1H-INDOLYL)-1H-INDOLE-2-CARBOXAMIDE DERIVATIVES

(75) Inventors: Laurent Dubois, Le Plessiss-Robinson (FR); Yannick Evanno, Dannemois (FR); Luc Even, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/109,388

(22) Filed: Apr. 25, 2008

(65) Prior Publication Data

US 2008/0227843 A1 Sep. 18, 2008

Related U.S. Application Data

(63) Continuation of application No. 11/624,406, filed on Jan. 18, 2007, now Pat. No. 7,384,969, which is a continuation of application No. PCT/FR2005/002014, filed on Aug. 2, 2005.

(30) Foreign Application Priority Data

Aug. 5, 2004 (FR) .................................. 04 08652

(51) Int. Cl.
*A61K 31/404* (2006.01)
*C07D 209/12* (2006.01)
*C07D 209/14* (2006.01)

(52) U.S. Cl. ...................................... 514/414; 548/460
(58) Field of Classification Search ................. 514/359, 514/408, 410, 412, 414; 548/460
See application file for complete search history.

(56) References Cited

U.S. PATENT DOCUMENTS

| 7,053,088 | B2 | 5/2006 | Doherty et al. | |
| 7,384,969 | B2 * | 6/2008 | Dubois et al. | 514/414 |
| 7,407,950 | B2 * | 8/2008 | Dubois et al. | 514/211.09 |
| 2005/0165049 | A1 | 7/2005 | Hulme et al. | |

FOREIGN PATENT DOCUMENTS

| WO | WO 03/049702 | 6/2003 |
| WO | WO 2004/072069 | 8/2004 |

OTHER PUBLICATIONS

Menendez, L., et. al., Analgesic Effects of Capsazepine and Resiniferatoxin on Bone Cancer Pain in Mice, Neuroscience Letters, vol. 393, (2006), pp. 70-73.
Nagy, et. al., The Role of the Vanilloid (Capsaicin) Receptor (TRPV1) in Physiology and Pathology, European Journal of Pharmacology, vol. 500, No. 1-3, pp. 351-369, (2004).
Szallasi, A., et. al., TRPV1: A Therapeutic Target For Novel Analgesic Drugs?, Trends in Molecular Medicine, vol. 12, No. 11, pp. 545-554, (2006).
Szallasi, A., et. al., The Vanilloid Receptor TRPV1: 10 Years from Channel Cloning and Antagonist Proof-of-Concept, Nature Reviews, Drug Discovery, vol. 6, pp. 357-372, (2007).

* cited by examiner

*Primary Examiner*—Kamal A Saeed
*Assistant Examiner*—Samantha L Shterengarts
(74) *Attorney, Agent, or Firm*—Balaram Gupta

(57) ABSTRACT

The invention relates to therapeutic use of compounds of general formula (I):

in which $X_1$, $X_2$, $X_3$, $X_4$, $X_5$, $Z_1$, $Z_2$, $Z_3$, $Z_4$ and $Z_5$, R, Y and n are as defined herein.

10 Claims, No Drawings

THERAPEUTIC USE OF N-(1H-INDOLYL)-1H-INDOLE-2-CARBOXAMIDE DERIVATIVES

CROSS REFERENCE TO RELATED APPLICATIONS

This application is a continuation of U.S. application Ser. No. 11/624,406, filed Jan. 18, 2007, now allowed, which is a continuation of International application No. PCT/FR2005/002,014, filed Aug. 2, 2005, both of which are incorporated herein by reference in their entirety; which claims the benefit of priority of French Patent Application No. 04/08,652, filed Aug. 5, 2004.

BACKGROUND OF THE INVENTION

1. Field of the Invention

A subject-matter of the invention is compounds derived from N-(1H-indolyl)-1H-indole-2-carboxamides which exhibit an in vitro and in vivo antagonist activity for receptors of TRPV1 (or VR1) type.

2. Description of the Art

Compounds disclosed in the document WO-A-03049702 of use in the treatment of diseases in which receptors of VR1 type are involved are already known, said reference is incorporated herein by reference in its entirety.

There still exists a need to find and develop products exhibiting a good in vivo activity.

The invention meets this aim by providing novel compounds which exhibit an in vitro and in vivo antagonist activity for receptors of VR1 type.

SUMMARY OF THE INVENTION

A first subject-matter of the invention is the compounds corresponding to the general formula (I) below.

Another subject-matter of the invention is processes for the preparation of the compounds of general formula (I).

Another subject-matter of the invention is the use of the compounds of general formula (I), in particular in medicaments or in pharmaceutical compositions.

The compounds of the invention correspond to the general formula (I):

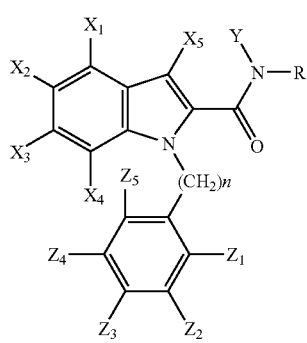

(I)

in which $X_1$, $X_2$, $X_3$, $X_4$, $Z_1$, $Z_2$, $Z_3$, $Z_4$ and $Z_5$ represent, independently of one another, a hydrogen or halogen atom or a $C_1$-$C_6$ alkyl, $C_3$-$C_7$ cycloalkyl, $C_1$-$C_6$ fluoroalkyl, $C_1$-$C_6$ alkoxy, $C_1$-$C_6$ fluoroalkoxy, cyano, $C(O)NR_1R_2$, nitro, $NR_1R_2$, $C_1$-$C_6$ thioalkyl, —S(O)—($C_1$-$C_6$)alkyl, —S(O)$_2$—($C_1$-$C_6$)alkyl, $SO_2NR_1R_2$, $NR_3COR_4$, $NR_3SO_2R_5$ or aryl group;

$X_5$ represents a hydrogen or halogen atom or a $C_1$-$C_6$ alkyl or $C_1$-$C_6$ fluoroalkyl group;

R represents a 4-, 5-, 6- or 7-indolyl group,

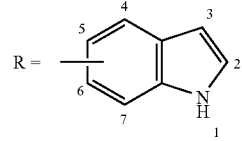

R optionally being substituted in the 1, 2 and/or 3 position by one or more groups chosen from $C_1$-$C_6$ alkyl and $C_1$-$C_6$ fluoroalkyl groups;

R optionally being substituted in the 4, 5, 6 and/or 7 position by one or more groups chosen from halogen atoms or $C_1$-$C_6$ alkyl, $C_1$-$C_6$ fluoroalkyl, $C_1$-$C_6$ alkoxy or $C_1$-$C_6$ fluoroalkoxy groups;

Y represents a hydrogen atom or a $C_1$-$C_6$ alkyl group;

n is equal to 0, 1, 2 or 3;

$R_1$ and $R_2$ represent, independently of one another, a hydrogen atom or a $C_1$-$C_6$ alkyl, $C_3$-$C_7$ cycloalkyl, ($C_3$-$C_7$)cycloalkyl($C_1$-$C_3$)alkyl or aryl group; or $R_1$ and $R_2$ form, together with the nitrogen atom which carries them, an azetidine, pyrrolidine, piperidine, azepine, morpholine, thiomorpholine, piperazine or homopiperazine group, this group optionally being substituted by a $C_1$-$C_6$ alkyl, $C_3$-$C_7$ cycloalkyl, ($C_3$-$C_7$) cycloalkyl($C_1$-$C_3$)alkyl or aryl group;

$R_3$ and $R_4$ represent, independently of one another, a hydrogen atom or a $C_1$-$C_6$ alkyl or aryl group;

$R_5$ represents a $C_1$-$C_6$ alkyl or aryl group.

DETAILED DESCRIPTION OF THE INVENTION

In the context of the present invention:

$C_t$-$C_z$, where t and z can take the values from 1 to 6, is understood to mean a carbon chain which can have from t to z carbon atoms, for example $C_1$-$C_3$ is understood to mean a carbon chain which can have from 1 to 3 carbon atoms;

an alkyl is understood to mean a saturated, linear or branched, aliphatic group. Mention may be made, by way of examples, of the methyl, ethyl, propyl, isopropyl, butyl, isobutyl, tert-butyl or pentyl groups, and the like;

a cycloalkyl is understood to mean a cyclic carbon group. Mention may be made, by way of examples, of the cyclopropyl, cyclobutyl, cyclopentyl or cyclohexyl groups, and the like;

a fluoroalkyl is understood to mean an alkyl group, one or more hydrogen atoms of which have been substituted by a fluorine atom;

an alkoxy is understood to mean an —O-alkyl radical where the alkyl group is as defined above;

a fluoroalkoxy is understood to mean an alkoxy group, one or more hydrogen atoms of which have been substituted by a fluorine atom;

a thioalkyl is understood to mean an —S-alkyl radical where the alkyl group is as defined above;

an aryl is understood to mean a cyclic aromatic group comprising between 6 and 10 carbon atoms. Mention may be made, by way of examples of aryl groups, of the phenyl or naphthyl groups;

a halogen atom is understood to mean a fluorine, a chlorine, a bromine or an iodine.

The compounds of formula (I) can exist in the form of bases or of addition salts with acids. Such addition salts form part of the invention.

These salts are advantageously prepared with pharmaceutically acceptable acids but the salts of other acids, of use, for example, in the purification or the isolation of the compounds of formula (I), also form part of the invention.

The compounds of general formula (I) can exist in the form of hydrates or of solvates, namely in the form of combinations or associations with one or more molecules of water or with a solvent. Such hydrates and solvates also form part of the invention.

Among the compounds of formula (I) which are subject-matters of the invention, a first subgroup of compounds is composed of the compounds for which:

$X_1, X_2, X_3, X_4, Z_1, Z_2, Z_3, Z_4$ and $Z_5$ represent, independently of one another, a hydrogen or halogen atom, more particularly a fluorine, a bromine or a chlorine, a $C_1$-$C_6$ alkyl group, more particularly a methyl, a propyl, an isopropyl, a sec-butyl, a tert-butyl or a pentyl, a $C_3$-$C_7$ cycloalkyl group, more particularly a cyclopentyl or a cyclohexyl, a $C_1$-$C_6$ fluoroalkyl group, more particularly a $CF_3$, a $C_1$-$C_6$ alkoxy group, more particularly a methoxy or an ethoxy, a $C_1$-$C_6$ fluoroalkoxy group, more particularly an $OCF_3$, a nitro group, an $NR_1R_2$ group, a $C_1$-$C_6$ thioalkyl group, more particularly a thiomethyl, an —S(O)—($C_1$-$C_6$)alkyl group, an —S(O)$_2$—($C_1$-$C_6$)alkyl group, more particularly an —S(O)$_2$—$CH_3$, or an aryl group, more particularly phenyl; and/or $X_5$ represents a hydrogen atom or a $C_1$-$C_6$ alkyl group, more particularly a methyl; and/or R represents a 4-, 5-, 6- or 7-indolyl group,

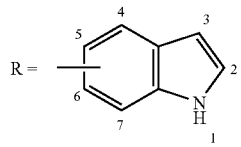

R optionally being substituted in the 1, 2 and/or 3 position by one or more $C_1$-$C_6$ alkyl groups, more particularly methyl or isopropyl groups; and/or Y represents a hydrogen atom; and/or n is equal to 0, 1, 2 or 3;

$R_1$ and $R_2$ represent, independently of one another, a hydrogen atom.

Among the compounds of formula (I) which are subject-matters of the invention, a second subgroup of compounds is composed of the compounds for which:

$X_1, X_2, X_3, X_4, Z_1, Z_2, Z_3, Z_4$ and $Z_5$ represent, independently of one another, a hydrogen or halogen atom, more particularly a fluorine, a bromine or a chlorine, a $C_1$-$C_6$ alkyl group, more particularly a methyl, a propyl, an isopropyl, a sec-butyl, a tert-butyl or a pentyl, a $C_3$-$C_7$ cycloalkyl group, more particularly a cyclopentyl or a cyclohexyl, a $C_1$-$C_6$ fluoroalkyl group, more particularly a $CF_3$, a $C_1$-$C_6$ alkoxy group, more particularly a methoxy or an ethoxy, a $C_1$-$C_6$ fluoroalkoxy group, more particularly an $OCF_3$, a nitro group, a $C_1$-$C_6$ thioalkyl group, more particularly a thiomethyl, an —S(O)—($C_1$-$C_6$)alkyl group, an —S(O)$_2$—($C_1$-$C_6$)alkyl group, more particularly an —S(O)$_2$—$CH_3$, or an aryl group, more particularly phenyl; and/or $X_5$ represents a hydrogen atom or a $C_1$-$C_6$ alkyl group, more particularly a methyl; and/or R represents a 4-, 5-, 6- or 7-indolyl group,

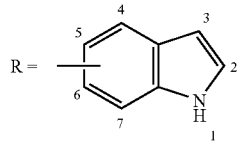

R optionally being substituted in the 1, 2 and/or 3 position by one or more $C_1$-$C_6$ alkyl groups, more particularly methyl groups; and/or Y represents a hydrogen atom; and/or n is equal to 0, 1, 2 or 3.

Among the compounds of formula (I) which are subject-matters of the invention, a third subgroup of compounds is composed of the compounds for which:

$X_1, X_2, X_3, X_4, Z_1, Z_2, Z_3, Z_4$ and $Z_5$ represent, independently of one another, a hydrogen or halogen atom or a $C_1$-$C_6$ alkyl, $C_3$-$C_7$ cycloalkyl, $C_1$-$C_6$ fluoroalkyl, $C_1$-$C_6$ alkoxy, $C_1$-$C_6$ fluoroalkoxy, cyano, C(O)$NR_1R_2$, nitro, $NR_1R_2$, $C_1$-$C_6$ thioalkyl, —S(O)—($C_1$-$C_6$)alkyl, —S(O)$_2$—($C_1$-$C_6$)alkyl, $SO_2NR_1R_2$, $NR_3COR_4$, $NR_3SO_2R_5$ or aryl group;

$X_5$ represents a hydrogen or halogen atom or a $C_1$-$C_6$ alkyl or $C_1$-$C_6$ fluoroalkyl group;

R represents a 4-, 5-, 6- or 7-indolyl group,

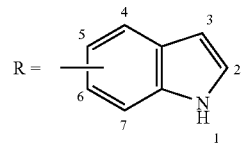

R optionally being substituted in the 1, 2 and/or 3 position by one or more groups chosen from $C_1$-$C_6$ alkyl and $C_1$-$C_6$ fluoroalkyl groups;

R optionally being substituted in the 4, 5, 6 and/or 7 position by one or more groups chosen from halogen atoms or $C_1$-$C_6$ alkyl, $C_1$-$C_6$ fluoroalkyl, $C_1$-$C_6$ alkoxy or $C_1$-$C_6$ fluoroalkoxy groups;

Y represents a hydrogen atom or a $C_1$-$C_6$ alkyl group;

n is equal to 0, 1, 2 or 3;

$R_1$ and $R_2$ represent, independently of one another, a hydrogen atom or a $C_1$-$C_6$ alkyl, $C_3$-$C_7$ cycloalkyl, ($C_3$-$C_7$)cycloalkyl($C_1$-$C_3$)alkyl or aryl group; or $R_1$ and $R_2$ form, together with the nitrogen atom which carries them, an azetidine, pyrrolidine, piperidine, azepine, morpholine, thiomorpholine, piperazine or homopiperazine group, this group optionally being substituted by a $C_1$-$C_6$ alkyl, $C_3$-$C_7$ cycloalkyl, ($C_3$-$C_7$) cycloalkyl($C_1$-$C_3$)alkyl or aryl group;

$R_3$ and $R_4$ represent, independently of one another, a hydrogen atom or a $C_1$-$C_6$ alkyl or aryl group;

$R_5$ represents a $C_1$-$C_6$ alkyl or aryl group; with the condition that, when $Z_1, Z_2, Z_3, Z_4$ and $Z_5$ simultaneously represent hydrogen atoms, then n is equal to 2 or 3.

Among the compounds of formula (I) which are subject-matters of the invention, a fourth subgroup of compounds is composed of the compounds for which:

R represents an indol-5-yl group

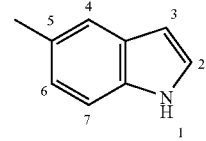

R optionally being substituted in the 1, 2 and/or 3 position by one or more groups chosen from $C_1$-$C_6$ alkyl and $C_1$-$C_6$ fluoroalkyl groups;

R optionally being substituted in the 4, 6 and/or 7 position by one or more groups chosen from halogen atoms or $C_1$-$C_6$ alkyl, $C_1$-$C_6$ fluoroalkyl, $C_1$-$C_6$ alkoxy or $C_1$-$C_6$ fluoroalkoxy groups;

$X_1, X_2, X_3, X_4, X_5, Z_1, Z_2, Z_3, Z_4, Z_5, Y, n, R_1, R_2, R_3, R_4$ and $R_5$ being as defined in the general formula (I) above or as defined in the first, the second or the third subgroup above.

Among the compounds of formula (I) which are subject-matters of the invention, a fifth subgroup of compounds is composed of the compounds for which:

$X_2$ and/or $X_3$ are other than a hydrogen atom;

$X_1, X_3, X_4, X_5, Z_1, Z_2, Z_3, Z_4, Z_5, R, Y, n, R_1, R_2, R_3, R_4$ and $R_5$ being as defined in the general formula (I) above or as defined in the first, the second, the third or the fourth subgroup above.

Among the compounds of formula (I) which are subject-matters of the invention, a sixth subgroup of compounds is composed of the compounds for which:

$X_5$ represents the hydrogen atom:

$X_1, X_2, X_3, X_4, Z_1, Z_2, Z_3, Z_4, Z_5, R, Y, n, R_1, R_2, R_3, R_4$ and $R_5$ being as defined in the general formula (I) above or as defined in the first, the second, the third, the fourth or the fifth subgroup above.

Among the compounds of formula (I) which are subject-matters of the invention, a seventh subgroup of compounds is composed of the compounds for which:

Y represents a hydrogen atom;

$X_1, X_2, X_3, X_4, X_5, Z_1, Z_2, Z_3, Z_4, Z_5, R, n, R_1, R_2, R_3, R_4$ and $R_5$ being as defined in the general formula (I) above or as defined in the first, the second, the third, the fourth, the fifth or the sixth subgroup above.

In accordance with the invention, the compounds of general formula (I) can be prepared according to the process illustrated by the following Scheme 1.

According to Scheme 1, the compounds of general formula (IV) can be obtained by reaction of a compound of general formula (II), in which $X_1, X_2, X_3, X_4$ Scheme I

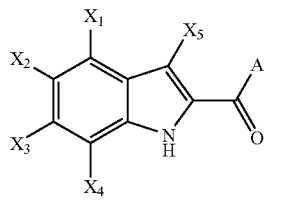

(II) A = $C_1$-$C_6$-alkoxy or OH

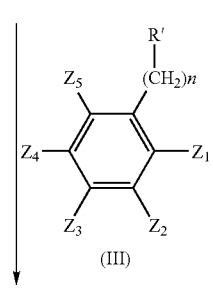

(III)

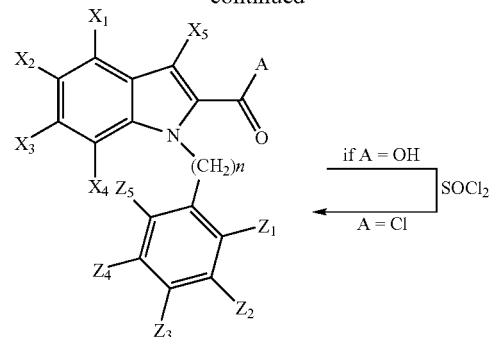

(IV) A = $C_1$-$C_6$-alkoxy, OH or halogen atom

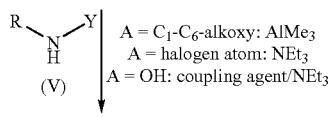

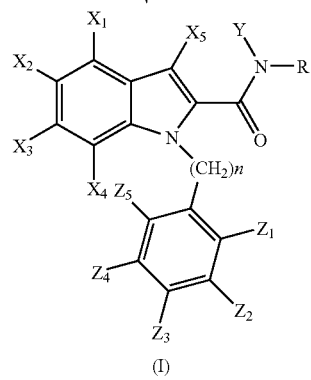

(I)

and $X_5$ are as defined in the general formula (I) above and A represents a $C_1$-$C_6$ alkoxy or hydroxyl group, with a compound of general formula (III), in which $Z_1, Z_2, Z_3, Z_4, Z_5$ and n are as defined in the general formula (I) above and R' represents a bromine or iodine atom, a tosylate group or any other equivalent group.

When n=1, 2 or 3, the compound of general formula (III) can be an alkyl halide, such as a benzyl bromide (n=1: Kolasa T., *Bioorg. Med. Chem.*, 1997, 5, (3) 507) or a phenethyl iodide (n=2: Abramovitch R., *Synth. Commun.*, 1995, 25 (1), 1), and the reaction can be carried out in the presence of a base, such as sodium hydride or potassium carbonate, in a polar solvent, such as dimethylformamide, dimethyl sulfoxide or acetone.

When n=0, the compound of general formula (III) is an aryl iodide or bromide and the reaction can be carried out at a temperature of between 80° C. and 250° C. in the presence of a copper-based catalyst, such as copper bromide or copper oxide, and of a base, such as potassium carbonate (Murakami Y., *Chem. Pharm. Bull.*, 1995, 43 (8), 1281). It is also possible to use milder conditions, described in S. L. Buchwald, *J. Am. Chem. Soc.*, 2002, 124, 11684.

Alternatively, the compounds of general formula (IV) in which n=0 can be obtained by reaction of the compound of general formula (II) with a compound of general formula (III) of boronic acid type (n=0, R'=B(OH)$_2$) in the presence of a base, such as triethylamine or pyridine, and of copper diacetate, by analogy with protocols described in W. W. K. R. Mederski, *Tetrahedron*, 1999, 55, 12757.

The compounds of general formula (II) are commercially available or are prepared according to numerous processes described in the literature (D. Knittel, *Synthesis*, 1985, 2, 186, and T. M. Williams, *J. Med. Chem.*, 1993, 36 (9), 1291, for example).

In the case of the indoles of general formula (IV) in which A represents a $C_1$-$C_6$ alkoxy group, the compound of general formula (I) is obtained by reaction of a compound of general formula (IV) as obtained above with an amide of the compound of general formula (V), in which R and Y are as defined in the general formula (I) above, at reflux of a solvent, such as toluene. The amide of the compound of general formula (V) is prepared by prior reaction of trimethylaluminum with the aminoindoles of general formula (V).

In the case of the indoles of general formula (IV) in which A represents a hydroxyl group, the carboxylic acid functional group can be converted beforehand to an acid halide, such as an acid chloride, by the action of thionyl chloride at reflux of a solvent, such as dichloromethane or dichloroethane. The compound of general formula (I) is then obtained by reaction of the compound of general formula (IV), in which A represents a chlorine atom, with the amino-indole of general formula (IV) in the presence of a base, such as triethylamine.

Alternatively, the indole of general formula (IV) in which A represents a hydroxyl group can be coupled to the aminoindole of general formula (V) in the presence of a coupling agent, such as a dialkylcarbodiimide, (benzotriazol-1-yloxy)tri-pyrrolidinophosphonium hexafluorophosphate, diethyl cyanophosphonate or any other coupling agent known to a person skilled in the art, in the presence of a base, such as triethylamine, in a solvent, such as dimethylformamide.

The aminoindoles of general formula (V) are prepared according to processes described in the literature, such as in I. T. Forbes, *J. Med. Chem.*, 1993, 36 (8), 1104 (Y=H), I. T. Forbes, WO9205170 (Y=alkyl).

In Scheme 1, the compounds of formulae (II), (III) and (V) and the other reactants, when their method of preparation is not described, are commercially available or are described in the literature or else can be prepared according to methods which are described therein or which are known to a person skilled in the art.

The compounds of general formulae (II), (IV) and (I) in which $X_1$, $X_2$, $X_3$, $X_4$, $X_5$, $Z_1$, $Z_2$, $Z_3$, $Z_4$ and/or $Z_5$ represent a cyano group or an aryl can be obtained by a coupling reaction, catalyzed by a metal such as palladium, carried out on the corresponding compounds of general formulae (II), (IV) or (I) in which $X_1$, $X_2$, $X_3$, $X_4$, $X_5$, $Z_1$, $Z_2$, $Z_3$, $Z_4$ and/or $Z_5$ represent a bromine atom.

The compounds of general formulae (II), (IV) and (I) in which $X_1$, $X_2$, $X_3$, $X_4$, $X_5$, $Z_1$, $Z_2$, $Z_3$, $Z_4$ and/or $Z_5$ represent a $C(O)NR_1R_2$ group can be obtained from the corresponding compounds of general formulae (II), (IV) or (I) in which $X_1$, $X_2$, $X_3$, $X_4$, $X_5$, $Z_1$, $Z_2$, $Z_3$, $Z_4$ and/or $Z_5$ represent a cyano group according to methods which are described in the literature or which are known to a person skilled in the art.

The compounds of general formulae (II), (IV) and (I) in which $X_1$, $X_2$, $X_3$, $X_4$, $X_5$, $Z_1$, $Z_2$, $Z_3$, $Z_4$ and/or $Z_5$ represent an S(O)-alkyl or $S(O)_2$-alkyl group can be obtained by oxidation of the corresponding compounds of general formulae (II), (IV) or (I) in which $X_1$, $X_2$, $X_3$, $X_4$, $X_5$, $Z_1$, $Z_2$, $Z_3$, $Z_4$ and/or $Z_5$ represent a $C_1$-$C_6$ thioalkyl group according to methods which are described in the literature or which are known to a person skilled in the art.

The compounds of general formulae (II), (IV) and (I) in which $X_1$, $X_2$, $X_3$, $X_4$, $X_5$, $Z_1$, $Z_2$, $Z_3$, $Z_4$ and/or $Z_5$ represent an $NR_1R_2$, $NR_3COR_4$ or $NR_3SO_2R_4$ group can be obtained from the corresponding compounds of general formulae (II), (IV) or (I) in which $X_1$, $X_2$, $X_3$, $X_4$, $X_5$, $Z_1$, $Z_2$, $Z_3$, $Z_4$ and/or $Z_5$ represent a nitro group, for example by reduction and then acylation or sulfonylation, according to methods which are described in the literature or which are known to a person skilled in the art.

The compounds of general formulae (II), (IV) and (I) in which $X_1$, $X_2$, $X_3$, $X_4$, $X_5$, $Z_1$, $Z_2$, $Z_3$, $Z_4$ and/or $Z_5$ represent an $SO_2NR_1R_2$ group can be obtained by a method analogous to that described in *Pharmazie*, 1990, 45, 346, or according to methods which are described in the literature or which are known to a person skilled in the art.

The following examples describe the preparation of some compounds in accordance with the invention. These examples are not limiting and only illustrate the present invention. The numbers of the compounds exemplified refer to those given in Table 1. The elemental microanalyses, the LC-MS (liquid chromatography coupled to mass spectrometry) analyses and the IR and NMR spectra confirm the structures of the compounds obtained.

Unless otherwise indicated, the chemical reactants used in the examples are all commercially available.

EXAMPLE 1

Compound No. 1

N-(1-Methyl-1H-indol-5-yl)-1-(3-trifluoromethylbenzyl)-1H-indole-2-carboxamide 1.1 Ethyl 1-(3-trifluoromethylbenzyl)-1H-indole-2-carboxylate A suspension of 0.492 g (2.6 mmol) of ethyl 1H-indole-2-carboxylate, of 0.683 g (2.86 mmol) of 3-trifluoromethylbenzyl bromide and of 0.898 g (6.5 mmol) of potassium carbonate in 50 ml of dimethylformamide is stirred at 60° C. for 24 hours. The reaction mixture is cooled and is poured into a mixture of ice-cold water and of ethyl acetate. After settling, the organic phase is separated and is then washed with two times 50 ml of water and then with 50 ml of a saturated sodium chloride solution. The solution is dried over magnesium sulfate and filtered, and then the filtrate is concentrated under reduced pressure. 0.8 g of an oil is obtained, which oil is used as is in the following stage.

1.2 N-(1-Methyl-1H-indol-5-yl)-1-(3-trifluoromethyl-benzyl)-1H-indole-2-carboxamide Compound No. 1

A solution of 0.231 g (1.58 mmol) of 1-methyl-1H-5-aminoindole (I. T. Forbes, *J. Med. Chem.*, 1993, 36 (8), 1104) in 15 ml of toluene is added dropwise at 0° C. to a solution of 0.93 ml (1.87 mmol) of trimethylaluminum (2M in toluene) in 6 ml of toluene. After stirring for 15 minutes, 0.5 g (1.44 mmol) of ethyl 1-(3-trifluoromethylbenzyl)-1H-indole-2-carboxylate, obtained in Stage 1.1, is added. The mixture is heated at 50° C. for 4 hours. The reaction mixture is subsequently hydrolyzed by addition of 10 ml of water and then it is taken up in 100 ml of ethyl acetate. The organic phase is washed with 100 ml of 1N hydrochloric acid, with two times 50 ml of water and then with 50 ml of a saturated sodium chloride solution. The solution is dried over magnesium sulfate and filtered, and then the filtrate is concentrated under reduced pressure. The residue is purified by chromatography on a silica column, elution being carried out with a mixture of cyclohexane and of dichloromethane, and then it is recrystallized from isopropanol. 0.33 g of product is thus obtained.
Melting point: 189-190° C.
$^1$H NMR (d$_6$-DMSO): δ (ppm): 3.75 (s, 3H), 5.93 (s, 2H), 6.38 (d, 1H), 7.4 (m, 11H), 7.71 (d, 1H), 7.96 (s, 1H).

EXAMPLE 2

Compound No. 2

N-(1-Methyl-1H-indol-5-yl)-5-methoxy-1-(3-trifluoro-methylbenzyl)-1H-indole-2-carboxamide 2.1 Ethyl 5-methoxy-1H-indole-2-carboxylate 1.91 ml (26.15 mmol) of thionyl chloride are added dropwise with stirring at 0° C. to a solution of 1 g (5.23 mmol) of 5-methoxy-1H-indole-2-carboxylic acid in 52 ml of ethanol. The reaction mixture is heated at reflux for 2 hours and then it is cooled and concentrated under reduced pressure. The residue is taken up in 100 ml of ethyl acetate and this solution is washed with two times 50 ml of water and then with 50 ml of a saturated sodium chloride solution. The solution is dried over magnesium sulfate and filtered, and then the filtrate is concentrated under reduced pressure. 1.2 g of product are obtained, which product is used as is in the following stage.

2.2 Ethyl 5-methoxy-1-(3-trifluoromethylbenzyl)-1H-indole-2-carboxylate

A solution of 1.2 g (5.47 mmol) of ethyl 5-methoxy-1H-indole-2-carboxylate, obtained in Stage 2.1, in 50 ml of dimethylformamide is added dropwise to a suspension of 0.306 g of sodium hydride in 10 ml of dimethylformamide. The mixture is stirred at ambient temperature for 1 hour, then 1.01 ml (6.57 mmol) of 3-trifluoromethylbenzyl bromide are added and stirring is maintained for an additional 4 hours. The reaction mixture is poured onto 200 ml of ice-cold water and 100 ml of ethyl acetate. After settling, the organic phase is separated and then it is washed with three times 50 ml of water and then with 50 ml of a saturated sodium chloride solution. The solution is dried over magnesium sulfate and filtered, and then the filtrate is concentrated under reduced pressure. 2 g of product are obtained, which product is used as is in the following stage.

2.3 N-(1-Methyl-1H-indol-5-yl)-5-methoxy-1-(3-trifluoromethylbenzyl)-1H-indole-2-carboxamide Compound No. 2

A solution of 0.278 g (1.91 mmol) of 1-methyl-1H-5-aminoindole (I. T. Forbes, *J. Med. Chem.*, 1993, 36 (8), 1104) in 15 ml of toluene is added dropwise at 0° C. to a solution of 1.59 ml (3.18 mmol) of trimethylaluminum (2M in toluene) in 10 ml of toluene. After stirring for 15 minutes, 0.6 g (1.59 mmol) of ethyl 5-methoxy-1-(3-trifluoromethylbenzyl)-1H-indole-2-carboxylate, obtained in Stage 2.2, is added. The mixture is heated at 50° C. for 4 hours. The reaction mixture is hydrolyzed by addition of 10 ml of water and then it is taken up in 100 ml of ethyl acetate. The organic phase is washed with 100 ml of 1N hydrochloric acid, with two times 50 ml of water and then with 50 ml of a saturated sodium chloride solution. The solution is dried over magnesium sulfate and filtered, and then the filtrate is concentrated under reduced pressure. The resulting product is purified by chromatography on a silica column, elution being carried out with a mixture of cyclohexane and of ethyl acetate, and then it is recrystallized from isopropanol. 0.55 g of product is obtained.
Melting point: 176-177° C.
$^1$H NMR (d$_6$-DMSO): δ (ppm): 3.8 (s, 3H), 3.89 (s, 3H), 5.9 (s, 2H), 6.49 (d, 1H), 7.2 (m, 8H), 7.48 (m, 2H), 7.9 (m, 2H).

EXAMPLE 3

Compound No. 3

N-(1-Methyl-1H-indol-5-yl)-5-fluoro-1-(3-fluorobenzyl)-1H-indole-2-carboxamide 3.1 Ethyl 5-fluoro-1-(3-fluorobenzyl)-1H-indole-2-carboxylate A suspension of 0.207 g (1 mmol) of ethyl 5-fluoro-1H-indole-2-carboxylate, 0.173 g (1.2 mmol) of 3-fluorobenzyl chloride and 0.276 g (2 mmol) of potassium carbonate in 10 ml of dimethylformamide is stirred at 60° C. for 24 hours. The reaction mixture is subsequently cooled and is poured into a mixture of ice-cold water and of ethyl acetate. After settling, the organic phase is separated and then it is washed with two times 50 ml of water and then with 50 ml of a saturated sodium chloride solution. The solution is dried over magnesium sulfate and is filtered, and then the filtrate is concentrated under reduced pressure. 0.195 g of an oil is obtained, which oil is used as is in the following stage.

3.2 N-(1-Methyl-1H-indol-5-yl)-5-fluoro-1-(3-fluoro-benzyl)-1H-indole-2-carboxamide Compound No. 3

A solution of 0.146 g (0.7 mmol) of 1-methyl-1H-5-aminoindole (I. T. Forbes, *J. Med. Chem.*, 1993, 36 (8), 1104) in 15 ml of toluene is added dropwise at 0° C. to a solution of 0.7 ml (1.4 mmol) of trimethylaluminum (2M in toluene) in 3 ml of toluene. After stirring for 15 minutes, 0.195 g (0.62 mol) of ethyl 5-fluoro-1-(3-fluorobenzyl)-1H-indole-2-carboxylate, obtained in Stage 3.1, is added. The mixture is heated at 50° C. for 4 hours. The reaction mixture is hydrolyzed by addition of 10 ml of water and then it is taken up in 100 ml of ethyl acetate. The organic phase is washed with 100 ml of 1N hydrochloric acid, with two times 50 ml of water and then with 50 ml of a saturated sodium chloride solution. The solution is dried over magnesium sulfate and filtered, and then the filtrate is concentrated under reduced pressure. The residue is purified by chromatography on a silica column, elution being carried out with a mixture of cyclohexane and of dichloromethane. 0.152 g of product is obtained.
Melting point=187-189° C.
$^1$H NMR (d$_6$-DMSO): δ (ppm): 3.77 (s, 3H), 5.87 (s, 2H), 6.38 (d, 1H), 7 (m, 4H), 7.32 (m, 7H), 7.98 (s, 1H).

EXAMPLE 4

Compound No. 30

N-(1-Methyl-1H-indol-5-yl)-1-(4-isopropylphenyl)-1H-indole-2-carboxamide 4.1 1-(4-Isopropylphenyl)-1H-indole-2-carboxylic acid A suspension of 128.8 g (0.8 mol) of 1H-indole-2-carboxylic acid, of 159.2 g (0.8 mol) of 4-bromocumene, of 111.6 g (0.808 mol) of potassium carbonate and of 8 g (0.1 mol) of copper oxide in 200 ml of dimethylformamide is stirred at reflux for 24 hours. After cooling, 6 l of water are added to the beige suspension obtained. The suspension is filtered and then the insoluble material is taken up in 1 l of a 5N hydrochloric acid solution. This mixture is extracted with 500 ml of dichloromethane. The organic phase is washed with water, dried over sodium sulfate and then concentrated under reduced pressure. After drying under reduced pressure, 204.4 g of a white solid are obtained, which solid is used as is in the following stage.

Melting point=203-204° C.

4.2 1-(4-Isopropylphenyl)-1H-indole-2-carbonyl chloride

A solution of 111 mg (0.4 mmol) of 1-(4-isopropylphenyl)-1H-indole-2-carboxylic acid, obtained in Stage 4.1, and of 90 ml (1.2 mmol) of thionyl chloride in 2 ml of dichloroethane is stirred at reflux for 3 hours. The reaction medium is concentrated under reduced pressure. A residue is obtained, which residue is used as is in the following stage.

4.3 N-(1-Methyl-1H-indol-5-yl)-1-(4-isopropylphenyl)-1H-indole-2-carboxamide Compound No. 30

A solution of 119 mg (0.4 mmol) of 1-(4-isopropylphenyl)-1H-indole-2-carbonyl chloride, obtained in Stage 4.2, 70 mg (0.48 mmol) of 1-methyl-1H-5-aminoindole and 110 ml (0.8 mmol) of triethylamine in 2 ml of tetrahydrofuran is stirred at ambient temperature for 18 hours. The reaction mixture is concentrated under reduced pressure and is taken up in 20 ml of water and 50 ml of dichloromethane. The organic phase is separated, washed with 50 ml of 1N hydrochloric acid, dried over magnesium sulfate and then concentrated under reduced pressure. The residue is purified by chromatography on a silica column, elution being carried out with a mixture of cyclohexane and of ethyl acetate. 0.133 g of product is obtained.

Melting point: 178-179° C.
$^1$H NMR (CDCl$_3$): δ (ppm): 1.39 (d, 6H), 3.05 (sept., 1H), 3.8 (s, 3H), 6.4 (d, 1H), 7.29 (m, 11H), 7.78 (m, 3H).

EXAMPLE 5

Compound No. 4

N-(1-Methyl-1H-indol-5-yl)-1-(3-trifluoromethylphenyl)-1H-indole-2-carboxamide

5.1 1-(3-Trifluoromethylphenyl)-1H-indole-2-carboxylic acid

The compound can be prepared according to a method analogous to that described in Stage 4.1 of Example 4, the 4-bromocumene being replaced with 3-bromo-α,α,α-trifluorotoluene.

5.2 N-(1-Methyl-1H-indol-5-yl)-1-(3-trifluoromethyl-phenyl)-1H-indole-2-carboxamide A solution of 2 g (6.55 mmol) of 1-(3-trifluoromethylphenyl)-1H-indole-2-carboxylic acid (prepared by analogy with the method described in Stage 4.1 of Example 4), 1.14 g (7.86 mmol) of 1-methyl-1H-5-aminoindole (I. T. Forbes, J. Med. Chem., 1993, 36 (8), 1104), 1.2 ml (7.86 mmol) of diethyl cyanophosphonate and 2.03 ml (14.41 mmol) of triethylamine in 20 ml of dimethylformamide is stirred at ambient temperature for 18 hours. The reaction mixtures is concentrated under reduced pressure and then it is taken up in 50 ml of water. This solution is extracted with two times 50 ml of dichloromethane. The organic phases are combined, dried over sodium sulfate and then concentrated under reduced pressure. The residue obtained is purified by chromatography on a silica column, elution being carried out with a mixture of cyclohexane and of ethyl acetate.

1.97 g of product are isolated.
Melting point: 225-226° C.
$^1$H NMR (d$_6$-DMSO): δ (ppm): 3.79 (s, 3H), 6.41 (d, 1H), 7.05 (d, 1H), 7.28 (m, 3H), 7.77 (m, 7H).

EXAMPLE 6

Compound No. 41

N-(1-Methyl-1H-indol-5-yl)-1-(3-isopropylphenyl)-5-trifluoromethyloxy-1H-indole-2-carboxamide

6.1 Ethyl 1-(3-isopropylphenyl)-5-trifluoromethyloxy-1H-indole-2-carboxylate A mixture of 0.2 g (0.73 mmol) of ethyl 5-trifluoromethyloxy-1H-indole-2-carboxylate, of 0.24 g (1.46 mmol) of 3-isopropylphenylboronic acid, of 0.2 g (1.1 mmol) of copper diacetate and of 0.12 ml (1.46 mmol) of pyridine in 5 ml of dichloromethane is stirred in the presence of 4 Å molecular sieve at ambient temperature for 4 days. The mixture is poured onto 100 ml of water and 50 ml of dichloromethane. The organic phase is separated, washed with 1N hydrochloric acid, dried over magnesium sulfate and then concentrated under reduced pressure. The residue is purified by chromatography on a silica column, elution being carried out with a mixture of cyclohexane and of ethyl acetate. 0.1 g of product is obtained, which product is used as is in the following stage.

6.2 N-(1-Methyl-1H-indol-5-yl)-1-(3-isopropylphenyl)-5-trifluoromethyloxy-1H-indole-2-carboxamide Compound No. 41

A solution of 0.0493 g (0.34 mmol) of 1-methyl-5-amino-1H-indole (I. T. Forbes, J. Med. Chem., 1993, 36 (8), 1104) in 5 ml of toluene is added dropwise at 0° C. to a solution of 0.28 ml (0.56 mmol) of trimethylaluminum (2M in toluene) in 2 ml of toluene. After stirring for 15 minutes, 0.1 g (0.28 mmol) of ethyl 1-(3-isopropylphenyl)-5-trifluoromethyloxy-1H-indole-2-carboxylate, obtained in Stage 6.1, is added. The mixture is heated at 50° C. for 4 hours. The reaction mixture is hydrolyzed by addition of 10 ml of water and then it is taken up in 100 ml of ethyl acetate. The organic phase is washed with 100 ml of 1N hydrochloric acid, with two times 50 ml of water and then with 50 ml of a saturated sodium chloride solution. The solution is dried over magnesium sulfate and filtered, and then the filtrate is concentrated under reduced pressure. The residue is purified by chromatography on a silica column, elution being carried out with a mixture of cyclohexane and of ethyl acetate, and then it is recrystallized from isopropanol. 0.136 g of product is obtained.

Melting point: 164-165° C.
$^1$H NMR (d$_6$-DMSO): δ (ppm): 1.22 (d×s, 6H), 2.98 (m, 1H), 3.79 (s, 3H), 6.38 (d, 1H), 7.4 (m, 11H), 7.9 (m, 2H).

EXAMPLE 7

Compound No. 70

N-(1H-Indol-5-yl)-5-fluoro-1-(3-fluorobenzyl)-1H-indole-2-carboxamide

A solution of 0.46 g (3.49 mmol) of 5-amino-1H-indole in 50 ml of toluene is added dropwise at 0° C. to a solution of 4.76 ml (9.51 mmol) of trimethylaluminum (2M in toluene) in 10 ml of toluene. After stirring for 15 minutes, 1 g (3.17 mmol) of ethyl 5-fluoro-1-(3-fluorobenzyl)-1H-indole-2-carboxylate, obtained in Stage 3.1 of Example 3, is added. The mixture is heated at 50° C. for 4 hours. The reaction mixture is hydrolyzed by addition of 10 ml of water and then it is taken up in 100 ml of ethyl acetate. The organic phase is washed with 100 ml of 1N hydrochloric acid, with two times 50 ml of water and then with 50 ml of a saturated sodium chloride solution. The solution is dried over magnesium sulfate and filtered, and then the filtrate is concentrated under reduced pressure. The residue is purified by chromatography on a silica column, elution being carried out with a mixture of cyclohexane and of dichloromethane. 0.7 g of product is obtained.

Melting point=158-163° C.

$^1$H NMR ($d_6$-DMSO): δ (ppm): 5.87 (s, 2H), 6.38 (m, 1H), 6.9 (m, 2H), 7.1 (m, 2H), 7.31 (m, 5H), 7.51 (m, 2H), 7.92 (s, 1H), 10.26 (s, 1H), 10.98 (s, 1H).

The chemical structures and the physical properties of a few compounds of general formula (I) according to the invention are illustrated in the following Table 1. In this table:

- the column "M.p." gives the melting points of the products in degrees Celsius (° C.). When the products have been isolated in the form of an amorphous solid or oil, they are characterized in this column by their mass ([MH]$^+$);
- Me, MeO, EtO, n-Pr, i-Pr, s-Bu and t-Bu respectively represent methyl, methoxy, ethoxy, propyl, isopropyl, sec-butyl and tert-butyl groups.

TABLE 1

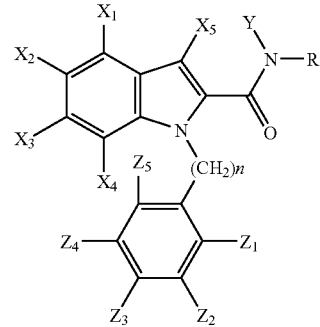

(I)

| No. | $X_1, X_2, X_3, X_4, X_5$ | R | Y | n | $Z_1$ | $Z_2$ | $Z_3$ | $Z_4$ | $Z_5$ | M.p. (° C.) |
|---|---|---|---|---|---|---|---|---|---|---|
| 1 | H, H, H, H, H | 1-Methylindol-5-yl | H | 1 | H | $CF_3$ | H | H | H | 189-190 |
| 2 | H, MeO, H, H, H | 1-Methylindol-5-yl | H | 1 | H | $CF_3$ | H | H | H | 176-177 |
| 3 | H, F, H, H, H | 1-Methylindol-5-yl | H | 1 | H | F | H | H | H | 187-189 |
| 4 | H, H, H, H, H | 1-Methylindol-5-yl | H | 0 | H | $CF_3$ | H | H | H | 225-226 |
| 5 | H, H, H, H, H | 1-Methylindol-5-yl | H | 0 | H | Me | H | Me | H | 142-144 |
| 6 | H, Me, H, H, H | 1-Methylindol-5-yl | H | 1 | H | $CF_3$ | H | H | H | 195-196 |
| 7 | H, H, H, H, H | 1-Methylindol-5-yl | H | 0 | H | H | H | H | H | 182-184 |
| 8 | H, H, MeO, H, H | 1-Methylindol-5-yl | H | 1 | H | $CF_3$ | H | H | H | 160-161 |
| 9 | H, Cl, H, H, H | 1-Methylindol-5-yl | H | 1 | H | $CF_3$ | H | H | H | 205-206 |
| 10 | MeO, H, H, H, H | 1-Methylindol-5-yl | H | 1 | H | $CF_3$ | H | H | H | 215-217 |
| 11 | H, F, H, H, H | 1-Methylindol-5-yl | H | 1 | H | $CF_3$ | H | H | H | 188-191 |
| 12 | H, F, H, H, H | 1-Methylindol-5-yl | H | 1 | H | H | $CF_3$ | H | H | 220-221 |
| 13 | H, F, H, H, H | 1-Methylindol-5-yl | H | 1 | H | $CF_3$ | H | H | Cl | 199-200 |
| 14 | H, F, H, H, H | 1-Methylindol-5-yl | H | 1 | H | Me | H | H | H | 161-163 |
| 15 | H, F, H, H, H | 1-Methylindol-5-yl | H | 1 | H | MeO | H | H | H | [MH]$^+$: 428 |
| 16 | H, F, H, H, H | 1-Methylindol-5-yl | H | 1 | H | $CF_3O$ | H | H | H | 173-174 |
| 17 | H, F, H, H, H | 1-Methylindol-5-yl | H | 1 | H | H | t-Bu | H | H | 217-218 |

TABLE 1-continued

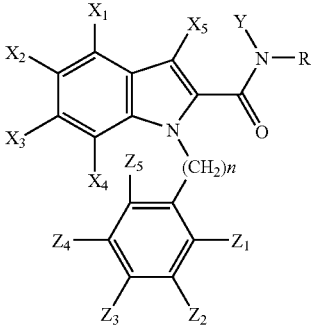

(I)

| No. | $X_1, X_2, X_3, X_4, X_5$ | R | Y | n | $Z_1$ | $Z_2$ | $Z_3$ | $Z_4$ | $Z_5$ | M.p. (° C.) |
|---|---|---|---|---|---|---|---|---|---|---|
| 18 | H, F, H, H, H | 1-Methylindol-5-yl | H | 1 | H | Cl | H | H | H | 171-172 |
| 19 | H, H, H, H, H | 1-Methylindol-5-yl | H | 0 | H | H | F | H | H | 224-225 |
| 20 | H, H, H, H, H | 1-Methylindol-5-yl | H | 0 | H | H | SMe | H | H | 73-74 |
| 21 | H, H, H, H, H | 1-Methylindol-5-yl | H | 0 | H | H | s-Bu | H | H | 191-192 |
| 22 | H, MeO, H, H, H | 1-Methylindol-5-yl | H | 0 | H | H | H | H | H | 166-168 |
| 23 | H, H, Me, H, H | 1-Methylindol-5-yl | H | 0 | H | H | i-Pr | H | H | 147-148 |
| 24 | H, H, H, H, H | 1-Methylindol-5-yl | H | 0 | H | H | n-pentyl | H | H | [MH]$^+$: 436 |
| 25 | H, H, H, H, H | 1-Methylindol-5-yl | H | 0 | H | H | cyclopentyl | H | H | 221-222 |
| 26 | H, H, H, H, H | 1-Methylindol-5-yl | H | 0 | H | H | Ph | H | H | 194-195 |
| 27 | H, H, H, H, H | 1-Methylindol-5-yl | H | 0 | H | H | $CF_3$ | H | H | 233-235 |
| 28 | H, H, H, H, H | 1-Methylindol-5-yl | H | 0 | H | H | n-Pr | H | H | 144-146 |
| 29 | H, H, H, H, H | 1-Methylindol-5-yl | H | 0 | H | Me | H | H | H | 86-88 |
| 30 | H, H, H, H, H | 1-Methylindol-5-yl | H | 0 | H | H | i-Pr | H | H | 178-179 |
| 31 | H, H, H, H, H | 1-Methylindol-5-yl | H | 0 | H | H | t-Bu | H | H | 169-170 |
| 32 | H, H, H, H, H | 1-Methylindol-5-yl | H | 0 | H | H | cyclohexyl | H | H | 227-229 |
| 33 | H, H, H, H, H | 1-Methylindol-5-yl | H | 0 | H | H | EtO | H | H | 94-95 |
| 34 | H, H, H, H, H | 1-Methylindol-5-yl | H | 0 | H | H | Cl | H | H | [MH]$^+$: 400 |
| 35 | H, F, H, H, H | 1-Methylindol-5-yl | H | 1 | H | F | H | F | H | [MH]$^+$: 434 |
| 36 | H, F, H, H, H | 1-Methylindol-5-yl | H | 1 | F | H | H | H | H | 204-206 |
| 37 | H, F, H, H, H | 1-Methylindol-5-yl | H | 1 | H | H | $CF_3O$ | H | H | 198-199 |
| 38 | H, F, H, H, H | 1-Methylindol-5-yl | H | 1 | H | H | Br | H | H | 209-210 |
| 39 | H, H, H, H, H | 1-Methylindol-5-yl | H | 0 | H | Me | Me | H | H | 148-150 |
| 40 | H, F, H, H, H | 1-Methylindol-5-yl | H | 2 | H | H | H | H | H | 158-159 |
| 41 | H, $CF_3O$, H, H, H | 1-Methylindol-5-yl | H | 0 | H | iPr | H | H | H | 164-165 |
| 42 | H, $CF_3$, H, H, H | 1-Methylindol-5-yl | H | 1 | H | $CF_3$ | H | H | H | 197-198 |
| 43 | H, F, H, H, H | 1-Methylindol-5-yl | H | 0 | H | $CF_3$ | H | H | H | 131-132 |
| 44 | H, $CF_3$, H, H, H | 1-Methylindol-5-yl | H | 1 | H | F | H | H | H | 181-182 |
| 45 | H, H, H, H, H | 1-Methylindol-6-yl | H | 0 | H | Me | H | Me | H | 161-163 |
| 46 | H, H, H, H, H | 1,2,3-Trimethylindol-5-yl | H | 0 | H | Me | H | Me | H | 179-181 |

TABLE 1-continued

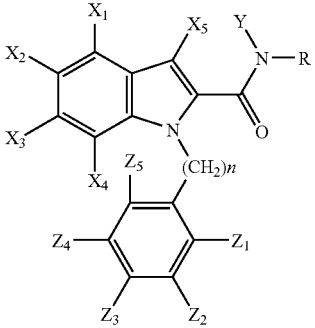

| No. | $X_1, X_2, X_3, X_4, X_5$ | R | Y | n | $Z_1$ | $Z_2$ | $Z_3$ | $Z_4$ | $Z_5$ | M.p. (° C.) |
|---|---|---|---|---|---|---|---|---|---|---|
| 47 | H, H, H, H, H | 1-Methylindol-4-yl | H | 0 | H | Me | H | Me | H | 94-106 |
| 48 | H, F, H, H, H | 1-Methylindol-6-yl | H | 1 | H | F | H | H | H | 173-175 |
| 49 | H, F, H, H, H | 1-Methylindol-7-yl | H | 1 | H | F | H | H | H | 153-155 |
| 50 | H, F, H, H, H | 1-Methylindol-5-yl | H | 2 | F | H | H | H | H | 187-188 |
| 51 | H, F, H, H, H | 1-Methylindol-5-yl | H | 2 | H | H | F | H | H | 198-199 |
| 52 | H, F, H, H, H | 1-Methylindol-5-yl | H | 3 | H | H | H | H | H | 177-178 |
| 53 | H, MeO, H, H, H | 1-Methylindol-5-yl | H | 1 | H | F | H | F | H | 165-166 |
| 54 | H, H, H, H, H | 1-Methylindol-7-yl | H | 0 | H | Me | H | Me | H | 180-182 |
| 55 | H, F, H, H, H | 1,2,3-Trimethylindol-5-yl | H | 1 | H | F | H | H | H | 183-185 |
| 56 | H, F, H, H, H | 1-Methylindol-4-yl | H | 1 | H | F | H | H | H | 197-199 |
| 57 | H, F, H, H, H | 1,2-Dimethylindol-5-yl | H | 1 | H | F | H | H | H | 206-208 |
| 58 | H, F, H, H, H | 1-Methylindol-5-yl | H | 2 | H | H | t-Bu | H | H | 182-184 |
| 59 | H, H, MeO, H, H | 1-Methylindol-5-yl | H | 1 | H | F | H | H | H | 202-205 |
| 60 | MeO, H, H, H, H | 1-Methylindol-5-yl | H | 1 | H | F | H | H | H | 177-179 |
| 61 | MeO, H, OMe, H, H | 1-Methylindol-5-yl | H | 1 | H | F | H | H | H | 183-185 |
| 62 | H, Cl, H, H, H | 1-Methylindol-5-yl | H | 1 | H | F | H | H | H | 201-202 |
| 63 | H, Me, H, H, H | 1-Methylindol-5-yl | H | 1 | H | F | H | H | H | $[MH]^+$: 412 |
| 64 | H, $SO_2Me$, H, H, H | 1-Methylindol-5-yl | H | 1 | H | F | H | H | H | 221-223 |
| 65 | H, $NO_2$, H, H, H | 1-Methylindol-5-yl | H | 1 | H | F | H | H | H | $[MH]^+$: 443 |
| 66 | H, F, H, H, H | 1-Isopropylindol-5-yl | H | 1 | H | F | H | H | H | 167-168 |
| 67 | F, H, H, H, H | 1-Methylindol-5-yl | H | 1 | H | F | H | H | H | 184-185 |
| 68 | H, iPr, H, H, H | 1-Methylindol-5-yl | H | 1 | H | F | H | H | H | 190-191 |
| 69 | H, $CF_3$, H, H, H | 1-Methylindol-5-yl | H | 1 | H | H | H | H | H | 193-194 |
| 70 | H, F, H, H, H | Indol-5-yl | H | 1 | H | F | H | H | H | 158-163 |
| 71 | H, $OCF_3$, H, H, H | 1-Methylindol-5-yl | H | 1 | H | F | H | H | H | 188-189 |
| 72 | Me, H, H, H, H | 1-Methylindol-5-yl | H | 1 | H | F | H | H | H | 204-205 |
| 73 | H, tBu, H, H, H | 1-Methylindol-5-yl | H | 1 | H | F | H | H | H | 209-210 |
| 74 | H, $NH_2$, H, H, H | 1-Methylindol-5-yl | H | 1 | H | F | H | H | H | 189-191 |

TABLE 1-continued (I)

[Structure: indole with substituents X1-X5 on benzene ring, position 2 has C(=O)-N(Y)-R, position 3 has X5, N has (CH2)n-phenyl with Z1-Z5]

| No. | $X_1, X_2, X_3, X_4, X_5$ | R | Y | n | $Z_1$ | $Z_2$ | $Z_3$ | $Z_4$ | $Z_5$ | M.p. (° C.) |
|---|---|---|---|---|---|---|---|---|---|---|
| 75 | H, H, Me, H, H | 1-Methylindol-5-yl | H | 1 | H | F | H | H | H | 206-208 |
| 76 | H, H, F, H, H | 1-Methylindol-5-yl | H | 1 | H | F | H | H | H | 230-231 |
| 77 | H, OMe, OMe, H, H | 1-Methylindol-5-yl | H | 1 | H | F | H | H | H | 243-246 |
| 78 | H, H, H, H, H | 1-Methylindol-5-yl | H | 1 | H | F | H | H | H | 185-186 |
| 79 | H, F, H, H, H | 1-Methylindol-5-yl | H | 1 | H | H | H | H | H | 193-194 |
| 80 | H, F, H, H, H | 1-Methylindol-5-yl | H | 2 | H | $CF_3$ | H | H | H | 172-173 |
| 81 | H, F, H, H, H | 1-Methylindol-5-yl | H | 2 | H | F | H | H | H | 178-180 |

The compounds of the invention have been subjected to in vitro and in vivo pharmacological trials which have demonstrated their advantage as substances possessing therapeutic activities.

Test of the Inhibition of the Current Induced by Capsaicin with Regard to Rat DRGs Primary Culture of Rat Dorsal Route Ganglion (DRG) Cells:

The neurons of the DRG naturally express the TRPV1 receptor.

Primary cultures of DRGs of newborn rats are prepared from 1-day-old rats. Briefly, after dissection, the ganglions are trypsinized and their cells dissociated mechanically by gentle trituration. The cells are resuspended in an Eagle's basal culture medium comprising 10% of foetal calf serum, 25 mM KCl, 2 mM glutamine, 100 µg/ml of gentamicin and 50 ng/ml of NGF and then deposited on glass cover slips covered with laminin (0.25×106 cells per cover slip) which are subsequently placed in 12-well Corning dishes. The cells are incubated at 37° C. in a humidified atmosphere comprising 5% of $CO_2$ and 95% of air. Cytosine β-D-arabinoside (1 µM) is added 48 h after culturing, in order to prevent the growth of non-neuronal cells. After culturing for 7-10 days, the cover slips are transferred into experimental chambers for the patch clamp studies.

Electrophysiology:

The measurement chambers (volume 800 µl) comprising the cell preparation are placed on the stage of an inverted microscope (Olympus IMT2) equipped with Hoffman optics (Modulation Contrast, New York) and are observed at a magnification of 400×. The chambers are continuously perfused by gravity (2.5 ml/min) using a distributor of solutions which has 8 inlets, the single outlet of which, composed of a polyethylene tube (opening 500 µm), is placed at least 3 mm from the cell studied. The "whole cell" configuration of the patch clamp technique was used. Borosilicate glass pipettes (resistance 5-10 Mohms) are brought close to the cell using a 3D piezoelectric micromanipulator (Burleigh, PC1000). The overall currents (membrane potential set at −60 mV) are recorded with an Axopatch 1D amplifier (Axon Instruments, Foster City, Calif.) connected to a PC controlled by Pclamp8 software (Axon Instruments). The current plots are recorded on paper and simultaneously recorded digitally (sampling frequency 15 to 25 Hz) and acquired on the hard disk of the PC.

The application of a 300 nM capsaicin solution produces an incoming cationic current with regard to the DRG cells (voltage set at −70 mV). In order to minimize the desensitization of the receptors, a minimum interval of one minute between two applications of capsaicin is observed. After a control period (stabilization of the capsaicin alone response), the test compounds are applied alone at a concentration of 10 nM for a period of time of 4 to 5 minutes, during which several capsaicin+compound tests are carried out (obtaining the maximum inhibition). The results are expressed as % of inhibition of the control capsaicin response.

The percentages of inhibition of the capsaicin (300 nM) response are between 20% and 100% for the most active compounds of the invention tested at a concentration of 10 nM (see some examples in Table 2).

The compounds of the invention are thus effective in vitro antagonists of receptors of TRPV1 type.

TABLE 2

| Compound No. | % Inhibition by the DRG patch technique |
| --- | --- |
| 1 | 56 |
| 11 | 48 |

Mouse Corneal Irritation Test

The irritating nature of capsaicin is easily assessed on the cornea since this organ is one of the most innervated by C fibers. In this context, according to preliminary experiments, the application of a very small amount of capsaicin (2 μl at a concentration of 160 μM) at the surface of the cornea of an animal results in a number of kinds of stereotyped behavior related to irritation which are easy to record. These include: blinking of the eye, rubbing of the instilled eye by the ipsilateral front paw, rubbing of the face with the two front paws and scratching of the ipsilateral face by the hind paw. The duration of these kinds of behavior does not exceed 2 minutes of observation and the animal then resumes its normal activity. Its appearance is furthermore also normal. The mouse does not hide in a corner with the hairs standing on end and does not develop any observable signs of suffering. It may be concluded therefrom that the duration of action of capsaicin at these doses is less than 2 minutes.

Summary of the Methodology:

The principle of the series of experiments is to determine whether the compounds of the invention can influence the behavioral response induced by a given amount of capsaicin. Capsaicin is initially diluted to 25 mM in DMSO and is diluted, for its final use, in 10% Tween 80 in physiological saline. It appears, from control studies, that the solvent has no effect under these conditions.

In practice, the test product is administered orally and, with a delay (pretreatment time: t) which depends on the pharmacokinetic data, the animal receives the ocular instillation of 2 μl of a 160 μM capsaicin solution prepared as indicated above. During observation for 2 minutes following the instillation, the number of rubbing actions on the instilled eye by the ipsilateral front paw is recorded.

For a given animal, the percentage of protection is calculated as follows:

$P=100-((\text{number of scratching actions observed}/\text{mean number of scratching actions of the group treated with the solvent})\times 100)$.

This percentage of protection is converted to a mean for each group of animals (n=number of animals tested with the compound of the invention).

The percentages of protection evaluated in this model for the most active compounds of the invention, used at a dose of 60 mg/kg (p.o.), are between 8% and 100% (see some examples in Table 3):

TABLE 3

| Compound No. | % P - (t) at 60 mg/kg (p.o.) - (n = 8) |
| --- | --- |
| 1 | 26% - (1 h) |
| 14 | 60% - (1 h) |

The results of these trials show that the most active compounds of the invention block the effects induced by the stimulation of the TRPV1 receptors.

The compounds of the invention can thus be used for the preparation of medicaments, in particular for the preparation of a medicament intended to prevent or to treat pathologies in which receptors of TRPV1 type are involved.

Thus, according to another of its aspects, a subject-matter of the invention is medicaments which comprise a compound of formula (I) or a pharmaceutically acceptable salt or also a hydrate or a solvate of the said compound.

These medicaments are employed in therapeutics, in particular in the prevention and/or the treatment of pain and inflammation, chronic, neuropathic (traumatic, diabetic, metabolic, infectious, toxic, induced by an anticancer treatment or iatrogenic), (osteo)arthritic or rheumatic pain, fibromyalgia, bone pain, cancer-related pain, trigeminal neuralgia, cephalgia, migraine, dental pain, burns, sunburn, bites or stings, post-herpetic neuralgia, muscle pain, nerve compression (central and/or peripheral), marrow and/or brain trauma, ischemia (of the marrow and/or brain), neurodegeneration, hemorrhagic vascular accidents (of the marrow and/or brain) or post-stroke pain.

The compounds of the invention can be used for the preparation of a medicament intended to prevent and/or to treat urological disorders, such as bladder hyperactivity, bladder hyperreflexia, bladder instability, incontinence, urgent urination, urinary incontinence, cystitis, renal colic, pelvic hypersensitivity and pelvic pain.

The compounds of the invention can be used for the preparation of a medicament intended to prevent and/or to treat gynecological disorders, such as vulvodynia, salpingitis-related pain or dysmenorrhea.

These products can also be used for the preparation of a medicament intended to prevent and/or to treat gastrointestinal disorders, such as gastro-oesophageal reflux disorder, stomach ulcers, duodenal ulcers, functional dyspepsia, colitis, IBS, Crohn's disease, pancreatitis, oesophagitis or biliary colic.

Likewise, the products of the present invention may be of use in the prevention and/or the treatment of respiratory disorders, such as asthma, coughs, COPD, bronchoconstriction and inflammatory disorders. These products can also be used to prevent and/or to treat psoriasis, pruritus, irritation of the skin, eyes or mucous membranes, herpes or shingles.

The compounds of the invention can also be used for the preparation of a medicament intended to treat depression.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of the said compound, and at least one pharmaceutically acceptable excipient.

The said excipients are chosen, according to the pharmaceutical form and the method of administration desired, from the usual excipients known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and human beings for the prophylaxis or the treatment of the disorders or diseases mentioned above.

The appropriate unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. The compounds according to the invention can be used, for topical application, in creams, gels, ointments or lotions.

By way of example, a unit administration form of a compound according to the invention in the tablet form can comprise the following components:

| Compound according to the invention | 50.0 mg |
|---|---|
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said unit forms comprise doses in order to make possible daily administration of 0.001 to 30 mg of active principle per kg of body weight, depending on the pharmaceutical dosage form.

There may be specific cases where higher or lower dosages are appropriate; such dosages do not depart from the scope of the invention. According to the usual practice, the dosage appropriate to each patient is determined by the physician according to the method of administration and the weight and response of the said patient.

The present invention, according to another of its aspects, also relates to a method for the treatment of the pathologies indicated above which comprises the administration, to a patient, of an effective dose of a compound according to the invention, or one of its pharmaceutically acceptable salts or hydrates or solvates.

What is claimed is:

1. A method of treating a disease selected from the group consisting of chronic inflammatory pain, neuropathic pain, migraine and acute pain, comprising administering to a patient in need of said treatment a therapeutically effective amount of a compound of formula (I) or a pharmaceutically acceptable salt thereof:

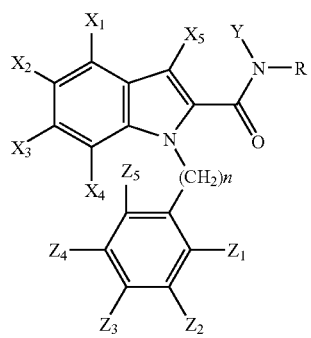

(I)

in which
$X_1$, $X_2$, $X_3$, $X_4$, $Z_1$, $Z_2$, $Z_3$, $Z_4$ and $Z_5$ represent, independently of one another, a hydrogen or halogen atom or a $C_1$-$C_6$ alkyl, $C_3$-$C_7$ cycloalkyl, $C_1$-$C_6$ fluoroalkyl, $C_1$-$C_6$ alkoxy, $C_1$-$C_6$ fluoroalkoxy, cyano, C(O)$NR_1R_2$, nitro, $NR_1R_2$, $C_1$-$C_6$ thioalkyl, —S(O)—($C_1$-$C_6$)alkyl, —S(O)$_2$—($C_1$-$C_6$)alkyl, SO$_2$$NR_1R_2$, $NR_3COR_4$, $NR_3SO_2R_5$ or aryl group;

$X_5$ represents a hydrogen or halogen atom or a $C_1$-$C_6$ alkyl or $C_1$-$C_6$ fluoroalkyl group;
R represents a 4-, 5-, 6- or 7-indolyl group,

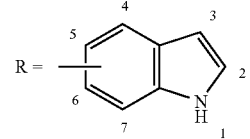

R optionally being substituted in the 1, 2 or 3 position by one or more groups chosen from the $C_1$-$C_6$ alkyl and $C_1$-$C_6$ fluoroalkyl groups;
R optionally being substituted in the 4, 5, 6 or 7 position by one or more groups chosen from halogen atoms or $C_1$-$C_6$ alkyl, $C_1$-$C_6$ fluoroalkyl, $C_1$-$C_6$ alkoxy or $C_1$-$C_6$ fluoroalkoxy groups;
Y represents a hydrogen atom or a $C_1$-$C_6$ alkyl group;
n is equal to 0, 1, 2 or 3;
$R_1$ and $R_2$ represent, independently of one another, a hydrogen atom or a $C_1$-$C_6$ alkyl, $C_3$-$C_7$ cycloalkyl, ($C_3$-$C_7$)cycloalkyl($C_1$-$C_3$)alkyl or aryl group; or
$R_1$ and $R_2$ form, together with the nitrogen atom which carries them, an azetidine, pyrrolidine, piperidine, azepine, morpholine, thiomorpholine, piperazine or homopiperazine group, said group optionally being substituted by $C_1$-$C_6$ alkyl, $C_3$-$C_7$ cycloalkyl, ($C_3$-$C_7$)cycloalkyl($C_1$-$C_3$)alkyl or aryl group;
$R_3$ and $R_4$ represent, independently of one another, a hydrogen atom or a $C_1$-$C_6$ alkyl or aryl group; and
$R_5$ represents a $C_1$-$C_6$ alkyl or aryl group.

2. The method according to claim 1, wherein the compound of formula (I) is having:
$X_1$, $X_2$, $X_3$, $X_4$, $Z_1$, $Z_2$, $Z_3$, $Z_4$ and $Z_5$ represent, independently of one another, a hydrogen or halogen atom or a $C_1$-$C_6$ alkyl, $C_3$-$C_7$ cycloalkyl, $C_1$-$C_6$ fluoroalkyl, $C_1$-$C_6$ alkoxy, $C_1$-$C_6$ fluoroalkoxy, nitro, $NR_1R_2$, $C_1$-$C_6$ thioalkyl, —S(O)—($C_1$-$C_6$)alkyl, —S(O)$_2$—($C_1$-$C_6$)alkyl or aryl group;
$X_5$ represents a hydrogen atom or a $C_1$-$C_6$ alkyl group;
R represents a 4-, 5-, 6- or 7-indolyl group,

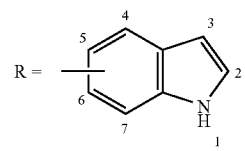

R optionally being substituted in the 1, 2 or 3 position by one or more $C_1$-$C_6$ alkyl groups;
Y represents a hydrogen atom;
n is equal to 0, 1, 2 or 3; and
$R_1$ and $R_2$ represent, independently of one another, a hydrogen atom.

3. The method according to claim 1, wherein the compound of formula (I) is having:
R represents an indol-5-yl group

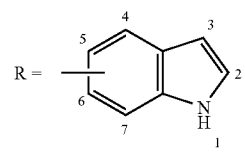

R optionally being substituted in the 1, 2 or 3 position by one or more groups chosen from $C_1$-$C_6$ alkyl and $C_1$-$C_6$ fluoroalkyl groups; and R optionally being substituted in the 4, 6 or 7 position by one or more groups chosen from halogen atoms or $C_1$-$C_6$ alkyl, $C_1$-$C_6$ fluoroalkyl, $C_1$-$C_6$ alkoxy or $C_1$-$C_6$ fluoroalkoxy groups.

4. The method according to claim 1, wherein $X_2$ or $X_3$ is other than a hydrogen atom.

5. The method according to claim 1, wherein $X_5$ represents a hydrogen atom.

6. The method according to claim 1, wherein Y represents a hydrogen atom.

7. The method according to claim 1, wherein the disease is chronic inflammatory pain.

8. The method according to claim 1, wherein the disease is neuropathic pain.

9. The method according to claim 1, wherein the disease is migraine.

10. The method according to claim 1, wherein the disease is acute pain.

* * * * *

UNITED STATES PATENT AND TRADEMARK OFFICE
CERTIFICATE OF CORRECTION

| | | |
|---|---|---|
| PATENT NO. | : 7,582,671 B2 | Page 1 of 1 |
| APPLICATION NO. | : 12/109388 | |
| DATED | : September 1, 2009 | |
| INVENTOR(S) | : Laurent Dubois et al. | |

It is certified that error appears in the above-identified patent and that said Letters Patent is hereby corrected as shown below:

In column 17-18, Table 1, col. 9, line 9, delete "F" and insert -- H --, therefor.

Signed and Sealed this
Eighteenth Day of January, 2011

David J. Kappos
*Director of the United States Patent and Trademark Office*